US012232738B2

(12) United States Patent
Perszyk et al.

(10) Patent No.: US 12,232,738 B2
(45) Date of Patent: Feb. 25, 2025

(54) FRAME AND PATCH DESIGN FOR OCCLUDER WITH ACCESS PASSAGE

(71) Applicant: St. Jude Medical, Cardiology Division, Inc., St. Paul, MN (US)

(72) Inventors: Brian Perszyk, Shoreview, MN (US); Erika Beek, Bloomington, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 18/500,321

(22) Filed: Nov. 2, 2023

(65) Prior Publication Data

US 2024/0065700 A1     Feb. 29, 2024

Related U.S. Application Data

(62) Division of application No. 17/165,487, filed on Feb. 2, 2021, now Pat. No. 11,839,381.

(60) Provisional application No. 62/969,561, filed on Feb. 3, 2020.

(51) Int. Cl.
*A61B 17/12* (2006.01)
*A61B 17/00* (2006.01)

(52) U.S. Cl.
CPC .. *A61B 17/12172* (2013.01); *A61B 17/12122* (2013.01); *A61B 17/12177* (2013.01); *A61B 2017/00862* (2013.01); *A61B 2017/00867* (2013.01)

(58) Field of Classification Search
CPC ........ A61B 17/12172; A61B 17/12122; A61B 17/12177; A61B 2017/00862
See application file for complete search history.

(56) References Cited

U.S. PATENT DOCUMENTS

| 2008/0262518 | A1 | 10/2008 | Freudenthal |
| 2011/0054519 | A1 | 3/2011 | Neuss |
| 2017/0224355 | A1* | 8/2017 | Bowman ................. B29C 71/02 |
| 2019/0000484 | A1* | 1/2019 | Zhuang .............. A61B 17/0057 |

FOREIGN PATENT DOCUMENTS

WO      2016038115 A1    3/2016

OTHER PUBLICATIONS

International Search Report and Written Opinion for International Patent Application No. PCT/US2021/016234, issued Aug. 12, 2021, 18 pages.

\* cited by examiner

*Primary Examiner* — Sarah A Long
*Assistant Examiner* — Raihan R Khandker
(74) *Attorney, Agent, or Firm* — Armstrong Teasdale LLP

(57) ABSTRACT

Braided occluding devices having an access passage and methods including the same are described herein. The occluding device includes a braided frame. The braided frame includes an annular distal disc portion, a waist member, and an annular proximal disc portion defining a passageway through the braided frame. The braided frame is formed with a closed end braid.

20 Claims, 16 Drawing Sheets

FRAME AND PATCH DESIGN FOR OCCLUDER WITH ACCESS PASSAGE

CROSS-REFERENCE TO RELATED APPLICATIONS

The present application is a divisional application of U.S. patent application Ser. No. 17/165,487, filed on Feb. 2, 2021, which claims the benefit of priority to U.S. Provisional Patent Application No. 62/969,561, filed Feb. 3, 2020, the entire contents of which are hereby incorporated by reference in their entirety.

BACKGROUND OF THE DISCLOSURE

A. Field of Disclosure

The present disclosure relates generally to medical devices used in the human body. In particular, the present disclosure is directed to frames and patch closures incorporated into medical devices delivered to a target site within the human body. More specifically, the present disclosure is directed to braided frames that may facilitate uniform loading and deployment of the medical devices, as well as reduce damage to cardiac tissue by reducing bulging of the deployed medical devices.

B. Background

Atrial Septal defects (ASD) include heart defects that allow blood to flow between the left and right atria of the heart (FIG. 1A), decreasing cardiac output. In at least some cases, ASD are closed using an occlusive closure device (FIG. 1B), such as the Amplatzer™ ASO (Atrial Septal Occluder). Occluders are generally formed from braided metal fabrics or wire with mesh. Some of these known occluders are shown in FIG. 1C, FIG. 1D, and FIG. 1E. As illustrated, conventional occluders 102 are formed with discs 104 that engage a surface of the septal wall that separates the left and right atria (FIG. 1B). These discs 104 can range in size from 10 mm to 54 mm in diameter and are conventionally formed of continuous metal fabric or wire. As such, these discs 104 form a substantially impenetrable surface.

With more and more procedures becoming percutaneous, there are several percutaneous procedures requiring access to the left atrium across the septal wall. For example, a younger patient may have an occluder deployed to close an ASD, but may subsequently develop atrial fibrillation (AFIB). A physician may need to map and/or ablate tissue in the left atrium, and may therefore need to cross the septal wall. Where a conventional occluder has already been deployed, the physician must navigate the web of metal fabric, wire, and/or mesh of the occluder in order to cross into the left atrium, and may be unable to penetrate the discs (e.g., discs 104 shown in FIGS. 1C-E) to cross the septal wall at the existing opening therethrough (i.e., the ASD). In such cases, the physician may need to remove the occluder in order to access the left atrium. Consequently, an occlusive device having an access passage may be used that both (i) provides an occlusive effect, and (ii) enables subsequent access through the passageway.

Tissue erosion after atrial septal defect closure is a known risk for occlusive medical devices. Erosion is a wearing away of the tissue due to the friction between the occluder and the tissue. The friction force can be lowered by making the occluder softer; however, a softer device is more prone to bulging into the atrium(s) as forces are applied to the waist and discs of the occluder. An occlusive device with an access passage may be prone to bulging due to the patch closure(s) that are applied to the device to provide the occlusive effect. Patch closures can bulge from the middle of the device without anything holding it in place. In conventional occluders, the continuous metal fabric/wire disc surfaces span the center of the device, thereby helping to contain the patches. Bulging may occur due to blood flow, or device compression/deformation. In some instances, a patch closure may facilitate loading and recapture of the device, however, if the patch closure has any permanent deformation, or pulls away from the disc edge, it has a propensity to bulge in the center of the device.

Accordingly, it would be desirable to have an access passage occlusive device that extends a minimal amount of metal into the access passage, outlines the septal defect to maximize tissue compliance of the device and minimize tissue erosion, and enables easier crossing for any subsequent passage of medical devices therethrough. It would further be desirable to reduce or eliminate bulging, and thereby reduce or eliminate erosion of cardiac tissue while maintaining the fundamental function and effectiveness of the patch closure(s) of an access passage occluder. Minimizing patch bulging is desirable to ensure there is a continuous surface for endothelialization and no pockets or voids that could be a source of thrombus formation.

BRIEF SUMMARY OF THE DISCLOSURE

The present disclosure generally relates to a closure design and patch design for closures and patches used in occluding devices that include an access passage. The present disclosure discloses such devices and methods of forming and using the same to, for example, enable uniform loading and deployment of the device, and to minimize bulging of the device and patch after the device has been deployed in the human body. The occluder having the access passage further facilitates access for medical devices therethrough as well as reduces erosion of cardiac tissue by reducing radial forces applied thereto.

In one embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is formed with a closed end braid.

In another embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of wire loops attached at every other wire group tail on at least one of the annular distal disc portion or the annular proximal disc portion. The radially inner surface of the annular distal disc portion, the waist member, and the radially inner surface of the annular proximal disc portion define an unobstructed passageway through the braided frame.

In one embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of formed wires each attached to a respective wire group tail and a center markerband on at least one of the annular distal disc portion or the annular proximal disc portion. The radially inner surface of the annular distal disc portion, the waist member, and the radially inner surface of the annular proximal disc portion define an unobstructed passageway through the braided frame.

In another embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is coated with at least one polymer coating.

In one embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is rolled over onto itself to form two layers of braid on at least one of the annular distal disc portion or the annular proximal disc portion.

In another embodiment, the present disclosure is directed to a method of eliminating or reducing erosion of cardiac tissue. The method comprises providing an occlusive medical device comprising: providing an occlusive medical device comprising: a braided frame comprising: an annular distal disc portion having a radially outer surface and a radially inner surface; an annular proximal disc portion having a radially outer surface and a radially inner surface; and a waist member extending between and connecting the annular distal disc portion to the annular proximal disc portion, wherein the radially inner surface of the annular distal disc portion, the waist member, and the radially inner surface of the annular proximal disc portion define an unobstructed passageway through the braided frame; and wherein the braided frame is formed with a plurality of formed wires in a closed end braid, each of the plurality of formed wires being attached to a respective wire group tail that extends radially inward past the closed end braid on at least one of the annular distal disc portion or the annular proximal disc portion; constraining the occlusive medical device in a reduced configuration; delivering the occlusive medical device; deploying the occlusive medical device such that the braided frame transitions from the reduced configuration to an expanded configuration; and increasing the occlusive medical device compliance on cardiac tissue.

In one embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and at least one patch closure. The radially inner surface of the annular distal disc portion, the waist member, and the radially inner surface of the annular proximal disc portion define an unobstructed passageway through the braided frame.

In one embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of braided wire spokes attached to a respective wire group tail and a center markerband on at least one of the annular distal disc portion or the annular proximal disc portion. The radially inner surface of the annular distal disc portion, the waist member, and the radially inner surface of the annular proximal disc portion define an unobstructed passageway through the braided frame.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

Figure 1A:
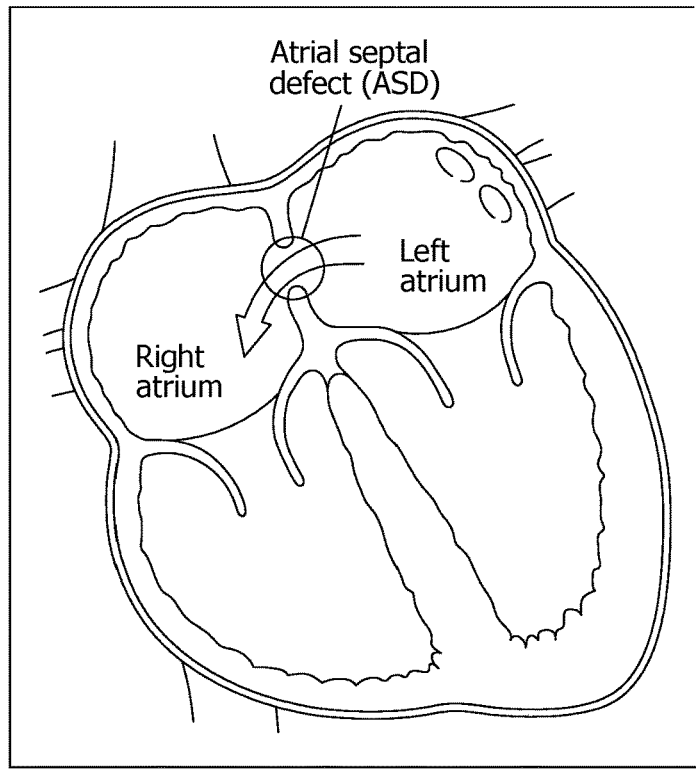
FIG. 1A illustrates an atrial septal defect (ASD).
Figure 1B:
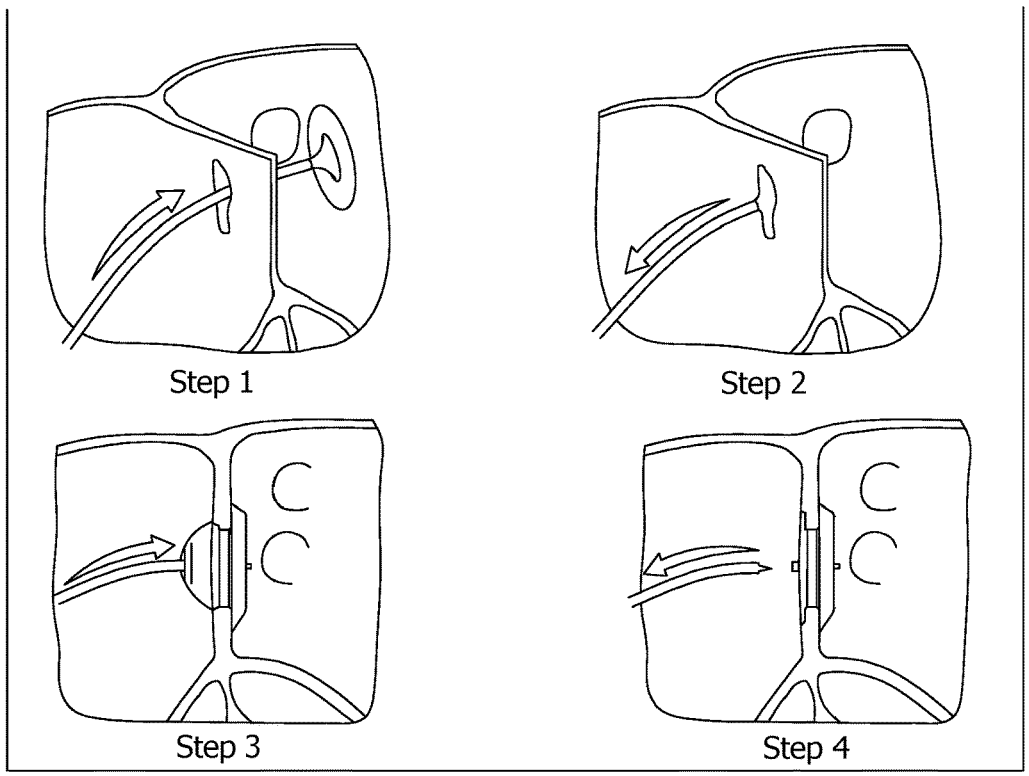
FIG. 1B illustrates a general closure procedure for an ASD with an occluding device.
Figures 1C, 1D, 1E:
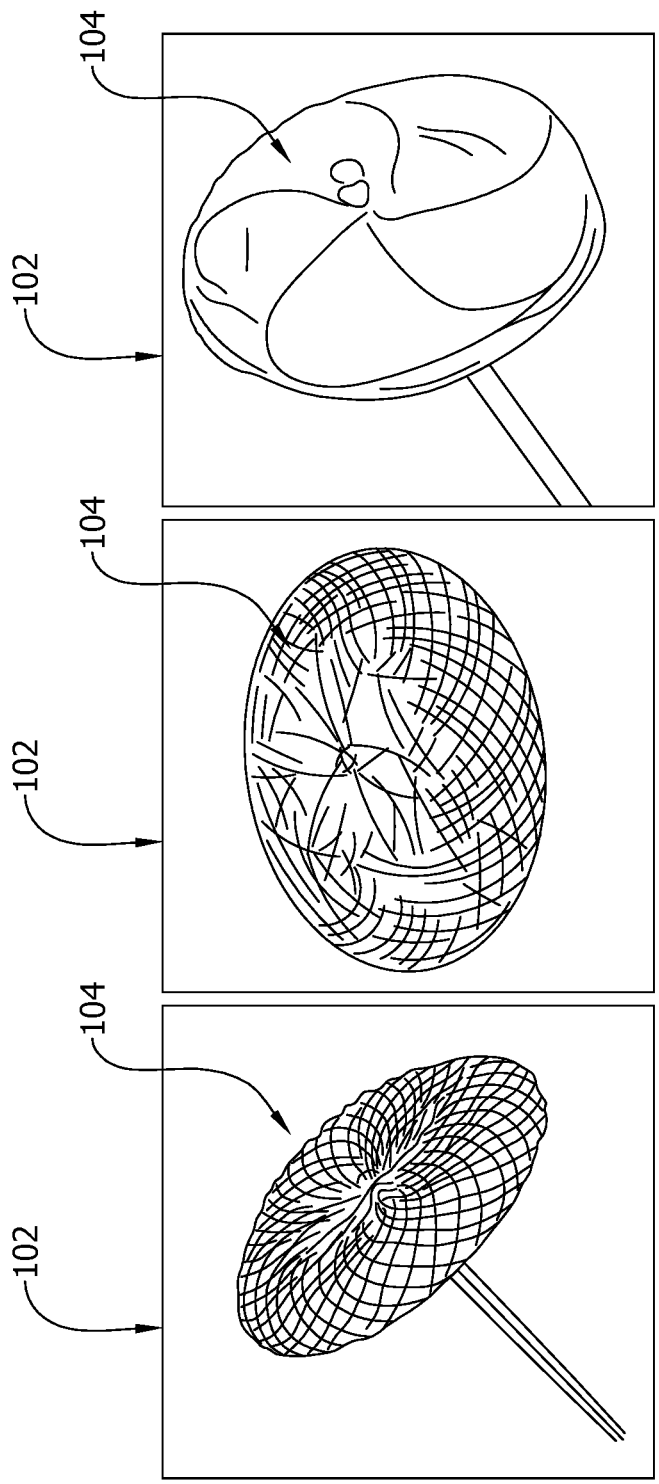
FIG. 1C, FIG. 1D, and FIG. 1E illustrate embodiments of conventional occluders.

The present disclosure relates generally to medical devices that are used in the human body. In particular, the present disclosure generally relates to loading and deployment considerations for occluders including an access passage for access through the occluder (e.g., by a medical device) subsequent to deployment of the occluder within a patient's body. The occluders also include a patch closure that serves an occlusion function but that is penetrable to allow access through the access passage. The patch may also enable fenestrations that can be created to offload the right heart for patients with pulmonary hypertension (a partial defect closure). As used herein, "access" refers broadly to access to and/or through the access passage by any medical device performing any function. Accordingly, "access" may refer to access by a medical device such as a catheter that is passed completely through the occluder, as well as to access by a medical device such as a device configured to create a fenestration in the occluder (e.g., a dilator, balloon, etc.).

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an LAA, an atrial septal defect, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout. Some embodiments of the present disclosure provide a medical device, such as an occlusion device (occluder), for use in occluding an abnormality in a patient's body, such as an Atrial Septal Defect (ASD), a Ventricular Septal Defect (VSD), a Patent Ductus Arteriosus (PDA), a Patent Foramen Ovale (PFO), conditions that result from previous medical procedures such as Para-Valvular Leaks (PVL) following surgical valve repair or replacement, and the like. The device may also be used as a flow restrictor or an aneurysm bridge or other type of occluder for placement in the vascular system. It is understood that the use of the term "abnormality" is not meant to be limiting, as the device may be configured to occlude any vessel, organ, opening, chamber, channel, hole, cavity, or the like, located anywhere in the body.

Some embodiments of the present disclosure provide an improved percutaneous catheter directed intravascular occlusion device for use in the vasculature in patients' bodies, such as blood vessels, channels, lumens, a hole through tissue, cavities, and the like, such as an ASD or VSD. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more occlusive materials, which are configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period. According to one embodiment of the present disclosure, the device is configured to occlude at least a portion of a vessel, a channel, a lumen, an opening, or a cavity in less than about 10 minutes and even less than about 5 minutes with observed occlusions in testing as low as within about 1 minute. Thus, in one embodiment, there is not "immediate occlusion," as the device does not immediately obstruct all blood flow but, rather, slows the flow of blood in order for occlusion to occur as described above. Such immediate occlusion may result in problems in fixation or positioning of the device in the lumen or may result in suction or the complete stoppage of flow which may be undesirable in some circumstances.

Figure 2:
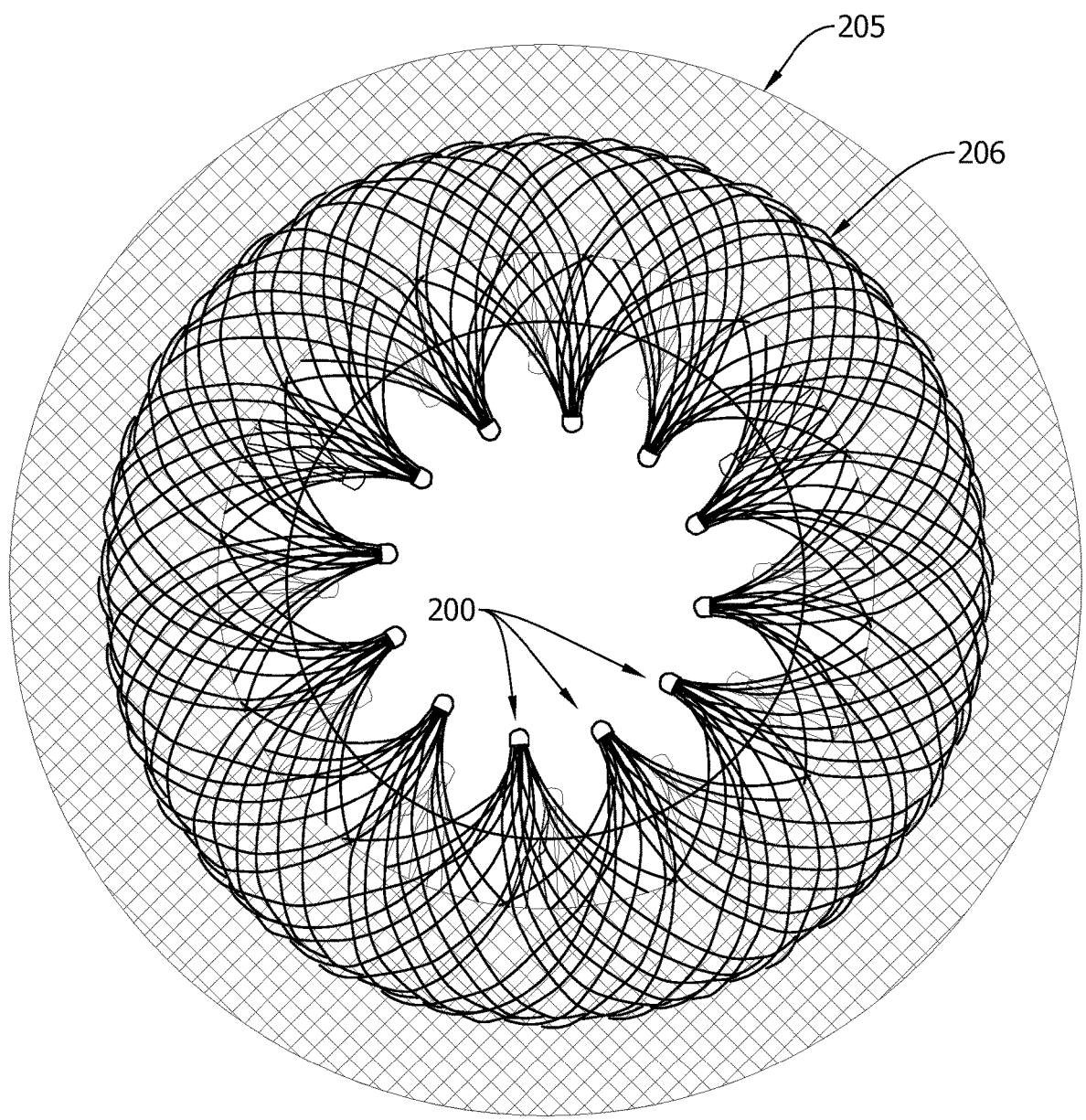
FIG. 2 is an exemplary embodiment of a braided occluder with access passage having wire groups on distal and proximal disc portions terminated in a markerband in accordance with the present disclosure.
Figure 3A:
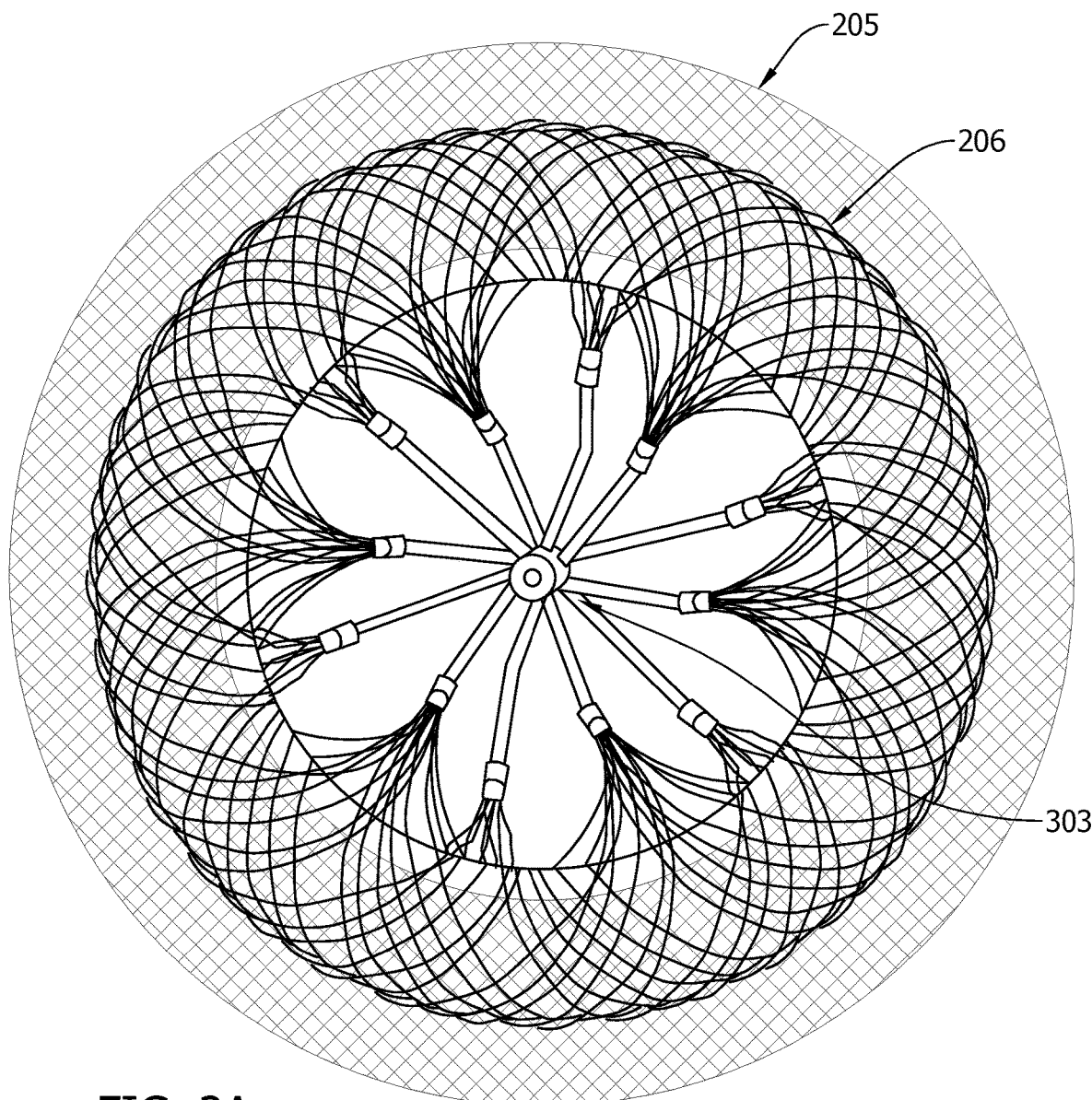
FIG. 3A is an exemplary embodiment of a braided occluder with access passage having an end screw sutured to an eyelet that is welded to each markerband in accordance with the present disclosure.
Figure 3B:
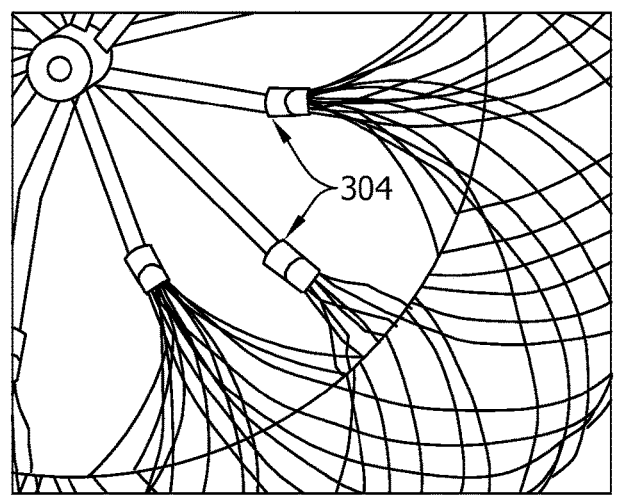
FIG. 3B depicts an enlarged view of the braided occluder shown in FIG. 3A.

As shown in FIG. 2, a braided occluder with access passage has the braid terminated approximately at the size of the waist of the device with 12 groups of 12 wires on each disc (distal disc 205 and proximal disc 206) being terminated in tails and capped with a markerband, shown as markerband tails 200. In this embodiment, the device is a 26 mm device with 144 wire braid, 40 mm diameter, and 12 groups of 12 wires (and consequently 12 markerband tails 200) on each disc. In this configuration, ensuring the tails on the proximal disc 206 all collapse and enter the loader or sheath at the same time may be difficult for a device having a stronger/stiffer braid, and the device may not collapse uniformly. Distal disc 205 also may not collapse well due to asymmetry or non-uniformity in the braid once the wires are grouped together and secured by their respective markerband. An additional problem resulting from non-uniform loading, is the tails on either disc crossing over and tangling with other tails on the same disc, which may cause the device to not fully deploy or come back to shape. In known medical devices, a strong braid (e.g., Nitinol braid) is used to prevent disc bulging. Ideally, a weaker/softer braid would reduce the risk of tissue erosion. Once deployed, the device may not conform to the anatomy as well. Disc bulging is not desirable as it can result in inadequate closure of the defect, and more mass inside of the anatomy (i.e., bulky devices are not preferred). Loading and deployment of this type of device was achieved, with some manipulation, in the configuration shown in FIG. 3A (for clarity, the 12 markerband tails 200 on distal disc 205 are not shown). In this embodiment, each markerband tail 200 (as shown in FIG. 2) on proximal disc 206 was modified by welding an eyelet to form markerband tail with eyelet 304, shown enlarged in FIG. 3B (for clarity, markerband tails 200 on distal disc 205 are not shown). Suturing an end screw 303 to each markerband tail with eyelet 304 facilitated delivery of the braided occluder via a delivery system (e.g., the Amplatzer™ Delivery System).

The medical devices of the present disclosure, which include braided occlusive devices having an access passage and patch closure(s), avoid at least these disadvantages of known medical devices.

Loading and Deployment

The embodiments described herein enable improved loading and deployment of the disclosed devices, which in turn enables improved device performance and treatment outcomes.

a. Closed End Braid

In an exemplary embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is formed with a closed end braid.

Closed end braid is a commonly known braid manufacturing technique. There is no knowledge of closed end braid being used on an occluder device. While a commonly known manufacturing technique, to Applicant's knowledge no closed end braid has been manufactured at a large diameter (30 mm or greater) and high number of wires (72 or greater) that is able to be collapsed down to a small diameter (14 French or smaller) for delivery through a sheath.

Utilizing a closed end braid to form the devices disclosed herein allows for braid symmetry and uniformity on the distal disc of the device, as well as decreasing the number of tails and amount of metal protruding into the center of the device Eliminating the distal tails removes the possibility of the tails entangling during loading and/or deployment, and also reduces the number of attachment points that can be a source of wire breaks and corrosion.

Figure 4A:
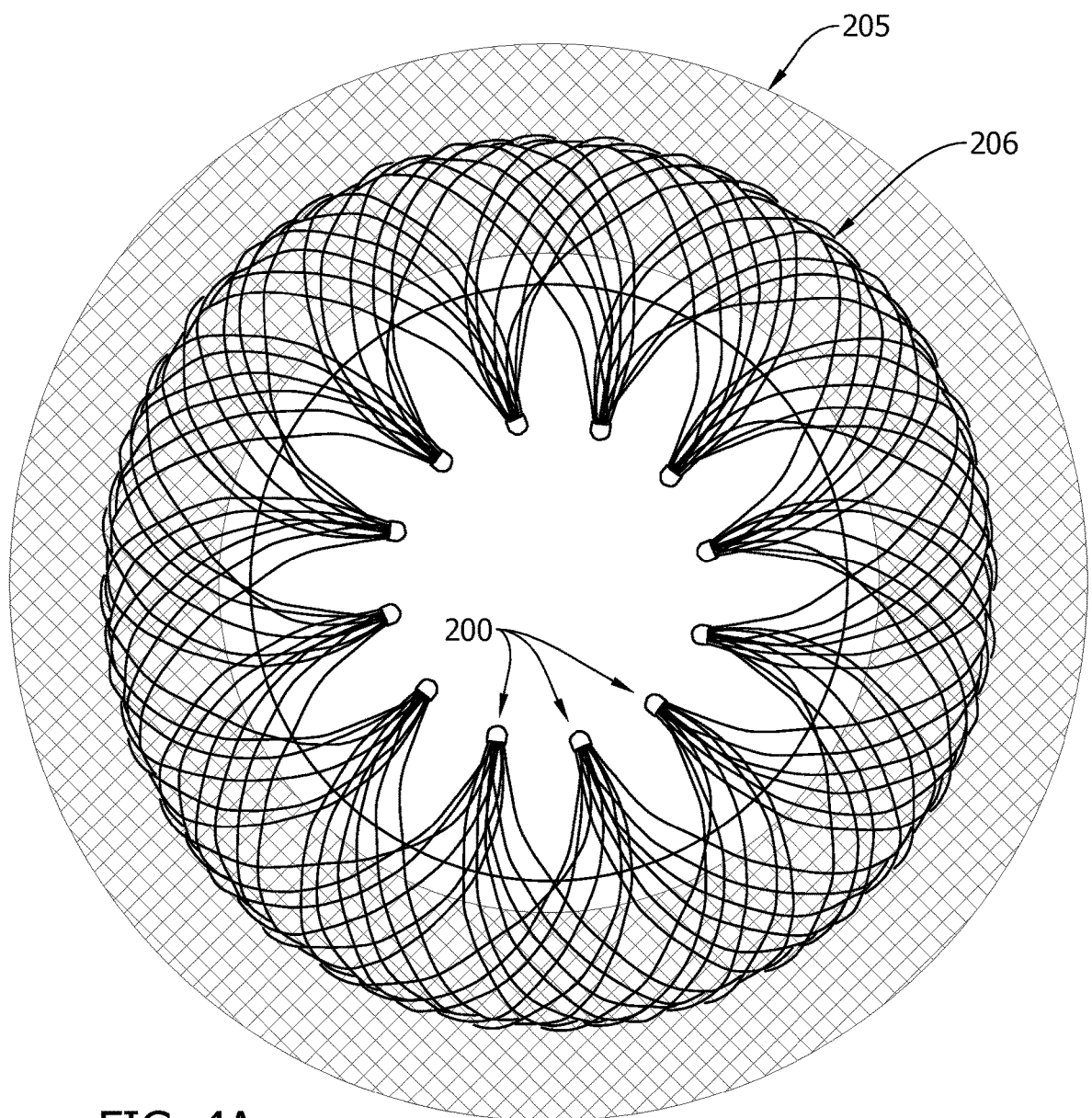
FIG. 4A is an exemplary embodiment of a braided occluder with access passage having a closed-end braid in accordance with the present disclosure.
Figure 4B:
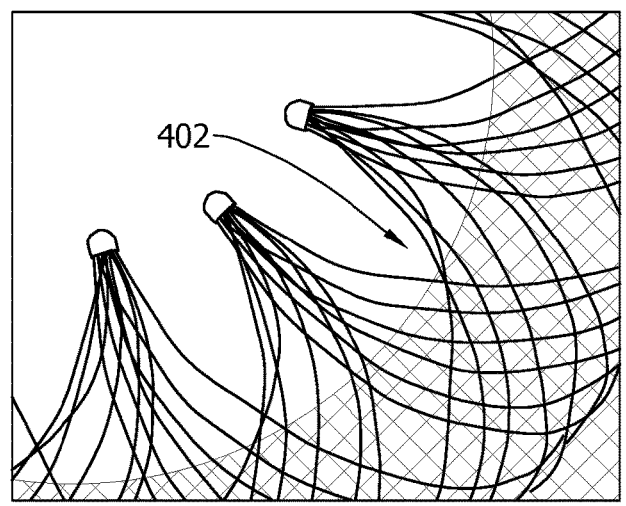
FIG. 4B depicts an enlarged view of the braided occluder shown in FIG. 4A.
Figure 5A:
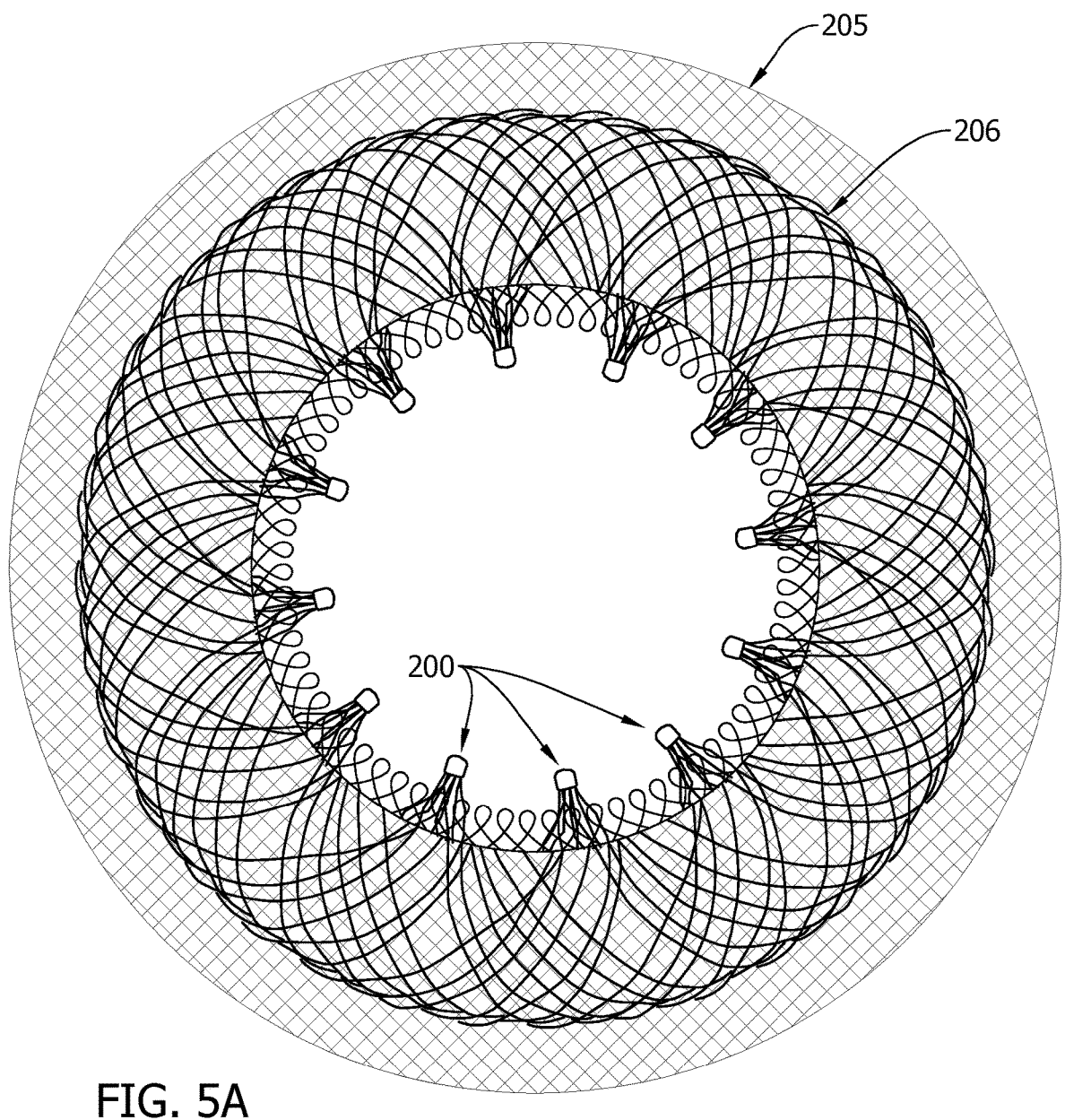
FIG. 5A is an exemplary embodiment of a braided occluder with access passage having a closed-end braid with loops in accordance with the present disclosure.
Figure 5B:
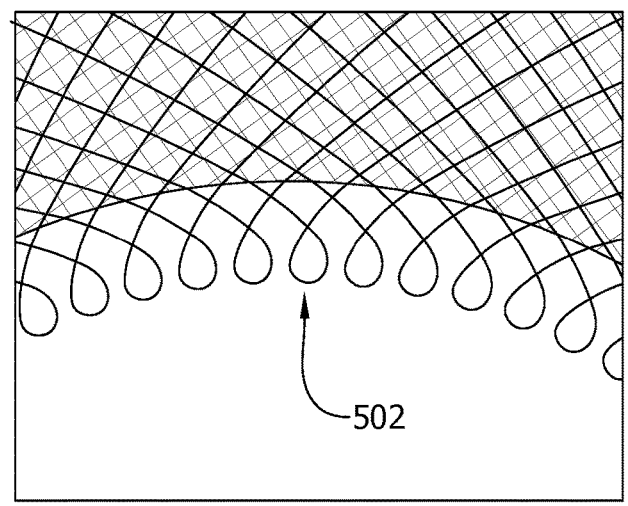
FIG. 5B depicts an enlarged view of the braided occluder shown in FIG. 5A.

Number of wires used, PPI (i.e., pics per inch, or the number of weft threads per inch), size of wire and size of pin used to form the closed end can all affect the ability of the closed end to collapse fully. FIG. 4A and FIG. 4B shows a device formed with a closed end braid 402, thus requiring no markerband tails on distal disc 205, as compared with a non-closed end braid shown in FIG. 2, FIG. 3A, and FIG. 3B having markerband tails 200 on both discs (note that markerband tails 200 on distal disc 205 are not shown in either FIG. 3A or FIG. 3B for clarity). In the non-closed braid configuration, the braid may collapse only to a certain diameter before unavoidably locking up, at which point the device may become entangled or need to fold to continue collapsing, both of which are undesirable because they increase the load force and the profile of the delivery system needed to collapse the device. Utilizing a closed end braid as further shown in the device in FIG. 5A and FIG. 5B with wire loops 502 (such as formed by wrapping wire around a pin (not shown) and creating loop 502) allowed the braid to collapse fully without locking up. This closed end braid design can be formed using any number of wires, loop size, or PPI.

b. Wire Loop Separators

In an exemplary embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of wire loops attached at every other wire group tail on at least one of the annular distal disc portion or the annular proximal disc portion. The radially inner surface of the annular distal disc portion, the waist member, and the radially inner surface of the annular proximal disc portion define an unobstructed passageway through the braided frame.

Figure 6:
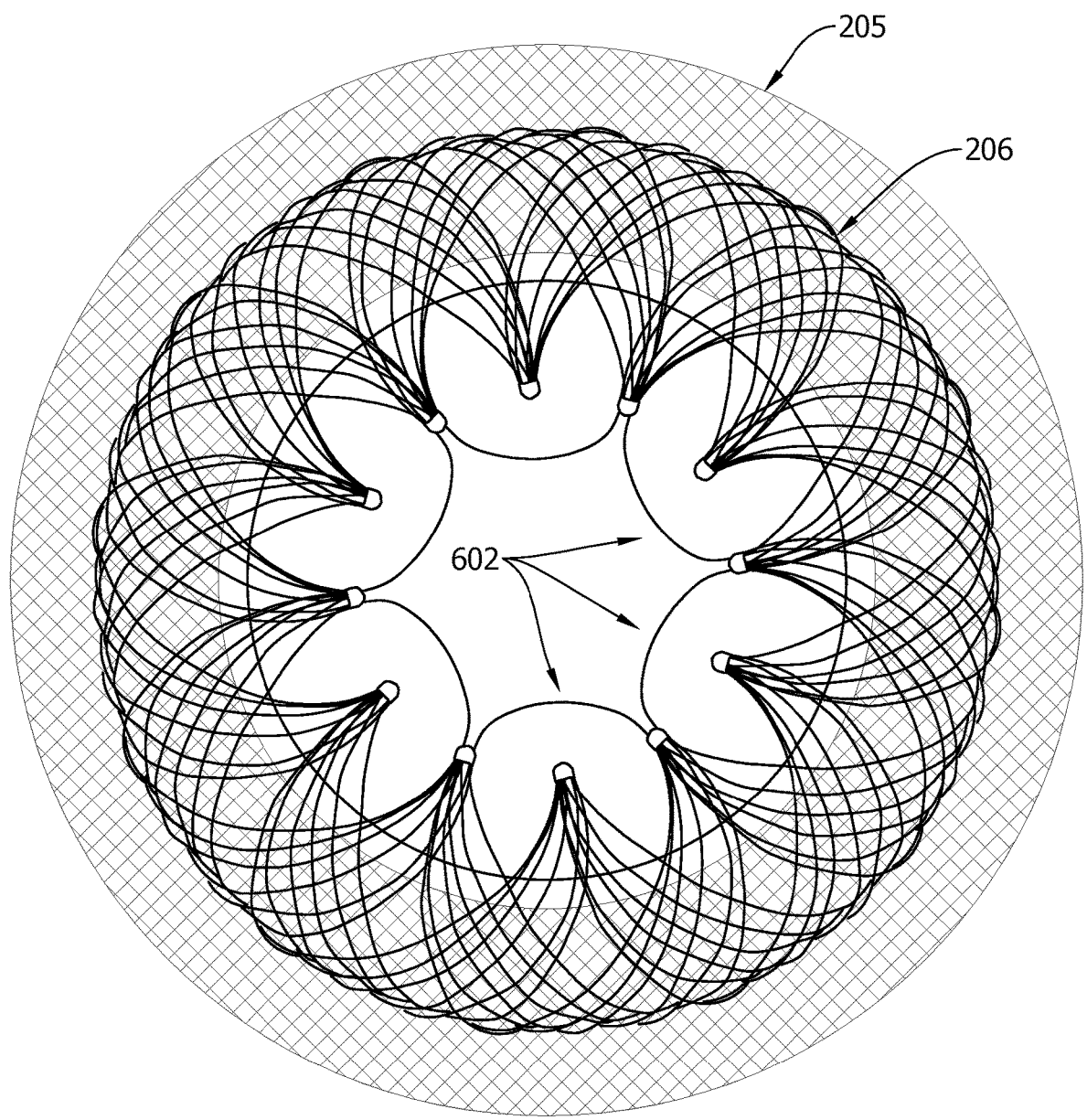
FIG. 6 is an exemplary embodiment of a braided occluder with access passage having wire loops on distal and proximal disc portions in accordance with the present disclosure.

In the embodiment shown in FIG. 6, wire loops 602 alternate attachment to the tails (i.e., loop attaches to every other tail in a clockwise or counterclockwise manner), thereby forcing the tails apart and ensuring they do not interfere with one another during loading and/or deployment. In this embodiment, six 0.0065" Nitinol wire loops are used on each disc. Wire loops of any form, size, or pattern may be utilized to maintain tail separation and accommodate successful loading and deployment. Depending on the embodiment, wire loops can attach to the tails in many different configurations (for example, to every tail group, or every third tail group, etc.).

c. Formed Wire Loops Extending to a Center Markerband

In an exemplary embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of formed wires each attached to a respective wire group tail and a center markerband on at least one of the annular distal disc portion or the annular proximal disc portion. The radially inner surface of the annular distal disc portion, the waist member, and the radially inner surface of the annular proximal disc portion define an unobstructed passageway through the braided frame.

Figure 7:
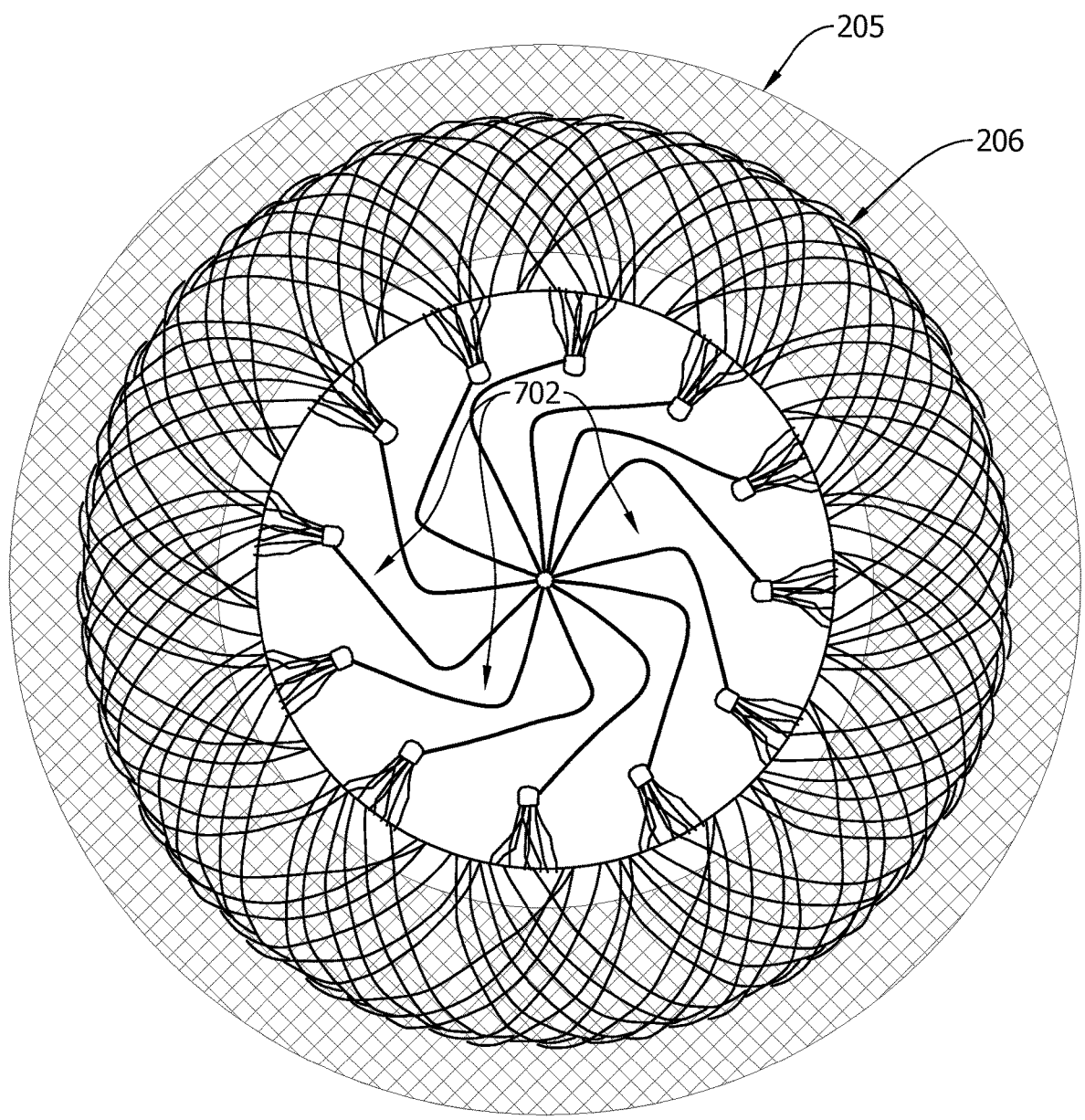
FIG. 7 is an exemplary embodiment of a braided occluder with access passage having wire loops on a proximal disc portion with each wire loop connecting each tail to a center markerband in accordance with the present disclosure.

In addition to maintaining tail separation as described above, formed wires may also act as a mechanism to load the device while maintaining the low radial stiffness of the access passage device. FIG. 7 shows a device with formed wire loops 702 in a spiral fashion welded into each markerband and coming together into a center markerband (which may be similar to, or used in conjunction with, end screw 303). In this embodiment, twelve 0.0065" Nitinol wire loops are used on the proximal disc 206, with each wire loop connecting a respective tail to the center markerband. Wire loops 702 together at the center markerband may also be used with an alternate cable attachment mechanism (e.g. ball and socket, tether, lasso) for loading and deployment. Wire forms in any shape that do not directly oppose one another across the device may be used to maintain compressibility and uniformity of the device.

d. Polymer Coating

In an exemplary embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is coated with at least one polymer coating.

Figure 8:
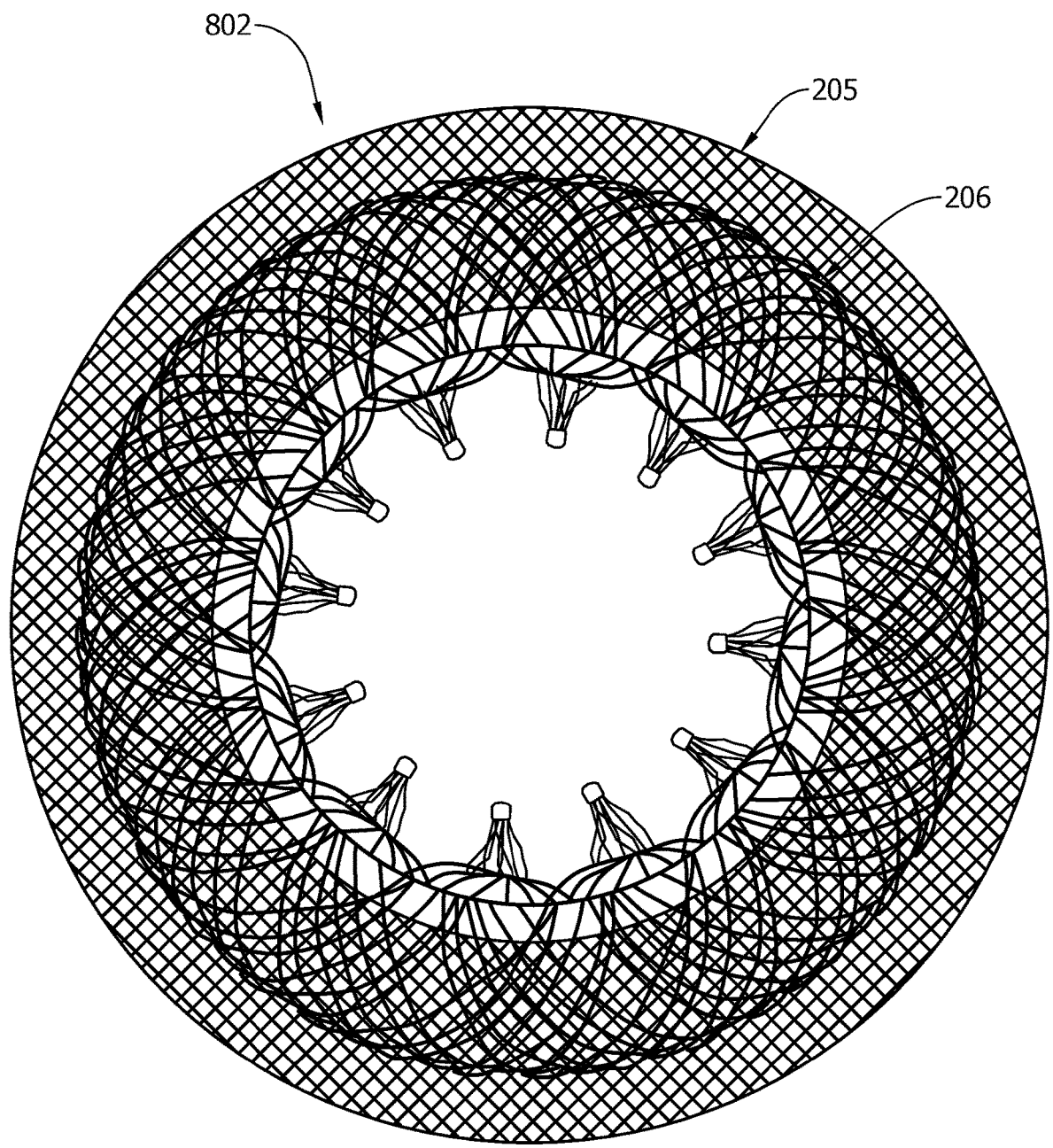
FIG. 8 is an exemplary embodiment of a polymer coated braided occluder with access passage in accordance with the present disclosure.

Access passage occlusive devices made with both high and low PPI braid deform upon loading, particularly as distal disc 205 is collapsed into the sheath. The deformation is worse in devices with a lower PPI as the devices are stiffer to pull down due to the wires taking a more direct path around the device. As a consequence, the wires tend to shift position relative to one another, causing wire bunching and deformation (e.g., "cobra deformation") as the device is collapsed into a loader or sheath. Adding a thin polymer coating across the wires in the device, particularly at the disc edge, locks the wires into position relative to one another, thereby decreasing the amount of deformation that occurs. FIG. 8 shows a thin layer of Polyurethane coating 802 applied over the braided device. Depending on the embodiment, any suitable polymer may be used to achieve the desired amount of wire/braid immobilization.

e. Rolled Over Braid

In an example embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, and a waist member extending between and connecting the annular distal disc portion to the annular proximal disc portion. The radially inner surface of the annular distal disc portion, the waist member, and the radially inner surface of the annular proximal disc portion define an unobstructed passageway through the braided frame. The braided frame is rolled over onto itself to form two layers of braid on at least one of the annular distal disc portion or the annular proximal disc portion.

Figure 9:
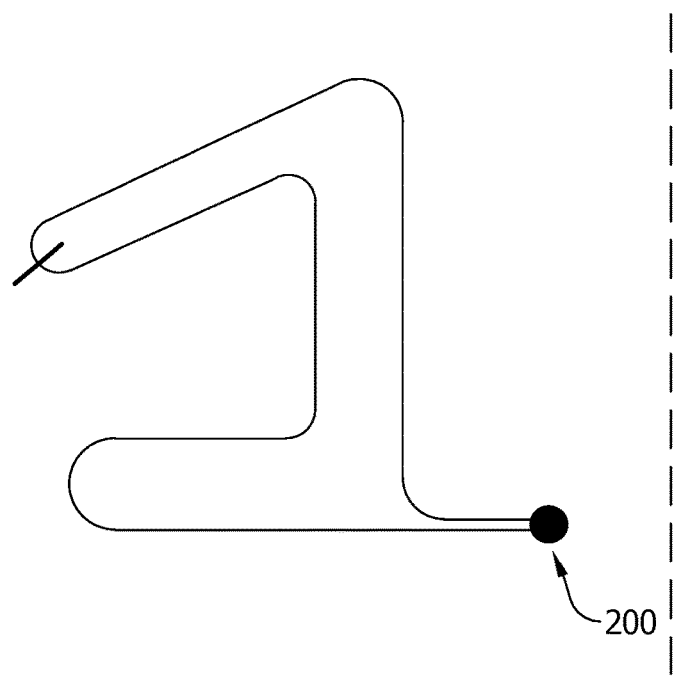
FIG. 9 is an exemplary embodiment of a cross-sectional view of an open-lumen occluder to demonstrate a rolled-over braid configuration (dotted line represents the open lumen) in accordance with the present disclosure.
Figure 10:
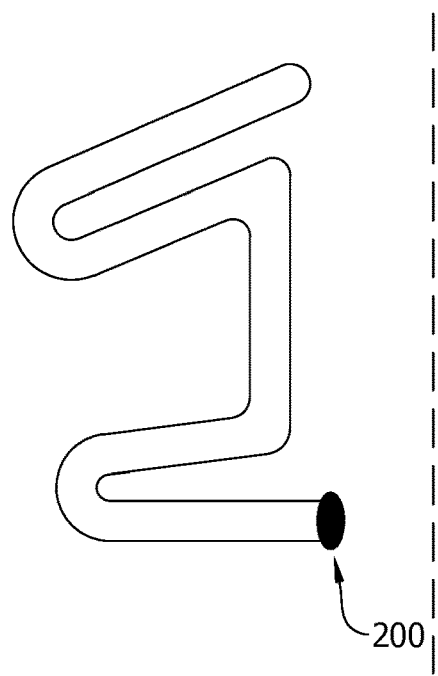
FIG. 10 is another exemplary embodiment of a cross-sectional view of an open-lumen occluder to demonstrate a rolled-over braid configuration (dotted line represents the open lumen) in accordance with the present disclosure.

Utilizing rolled over braid to form the devices of the present disclosure allows for braid symmetry and uniformity on the distal disc of the device, as well as decreasing the number of tails and amount of metal protruding into the center of the device. The symmetry in the braid throughout the device allows the device to collapse better and more uniformly. FIG. 9 and FIG. 10 show potential braid path configurations relative to markerband tails 200 for producing and using a rolled over braid. Having an increased PPI in the braid beginning at the disc edge or further toward the inside of the device accommodates the difference in braid layer length upon collapsing of the device (e.g., a reduced configuration of the device) so the distal disc edge collapses into the sheath last. Additionally, having the braid turn back into the center and towards the opposite disc minimizes bulging and accordingly reduces the risk for tissue erosion of the deployed device.

f. Methods of Using the Device

In accordance with the present disclosure, the occlusive medical devices disclosed herein are directed toward methods of eliminating or reducing erosion of cardiac tissue. The methods comprise providing an occlusive medical device comprising a braided frame, the braided frame comprising an annular distal disc portion having a radially outer surface and a radially inner surface, an annular proximal disc portion having a radially outer surface and a radially inner surface, and a waist member extending between and connecting the annular distal disc portion to the annular proximal disc portion; wherein the radially inner surface of the annular distal disc portion, the waist member, and the radially inner surface of the annular proximal disc portion define an unobstructed passageway through the braided frame; constraining the occlusive medical device from a preset expanded configuration to a reduced configuration; delivering the occlusive medical device; deploying the occlusive medical device such that the frame returns to the preset expanded configuration; and, increasing the occlusive medical device compliance on cardiac tissue.

Patch Bulging Mitigation

The embodiments disclosed herein mitigate patch closure bulging in the middle of the device via a patch design, and/or patch support by the device, while maintaining the majority of the non-braided surface area in the middle of the device (i.e., within the access passage).

In an exemplary embodiment of an access passage occluder, such as those shown in FIGS. 2-8 and 11, at least one patch or patch closure (not shown) is attached to a frame of the occlusive device to close or restrict access (e.g., of bodily fluids) through the passageway (i.e., access passage)

of the occluder. In this way, the patch closure(s) ensures the occluder performs its occlusive function, as described above herein. However, the patch closure is formed from an occlusive, yet penetrable material, such that access through the passageway of the occluder by medical devices is not restricted. In the exemplary embodiment, a "penetrable" material is more easily punctured, separated, slit, pierced, or otherwise penetrated than the material that forms the frame.

In some embodiments, patch closure(s) are operable in tandem with the braided frame of the device during deployment (including loading, advancement, and/or recapture) of the occluder, such that the patch closure(s) collapse and expand as the frame collapses and expands (i.e., when the frame transitions between a reduced configuration to an expanded configuration). In an exemplary embodiment the patch closure is flexible, thus simplifying deployment of the occluder and improving the penetrability of the patch closure (particularly when contrasted with the more rigid, dense conventional metal wire/mesh that forms the distal and proximal discs 205 and 206, respectively).

a. Patch Design

In an exemplary embodiment, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and at least one patch closure. The radially inner surface of the annular distal disc portion, the waist member, and the radially inner surface of the annular proximal disc portion define an unobstructed passageway through the braided frame.

The patch closure may be formed from any suitable material. It is contemplated that a bioabsorbable material that promotes endothelialization may be used to form the patch closure. After the occluder is deployed, the bioabsorbable material will be absorbed while tissue grows over the occluder. Therefore, the passageway (or access passage) will be accessible through a relatively soft, thin layer of tissue. Such bioabsorbable materials may include polylactic acid (PLA), poly-L-lactic acid (PLLA), poly lactic-co-glycolic acid (PLGA), polycaprolactone (PCL), combinations thereof, and/or any suitable bioabsorbable material. Alternatively, the patch closure is at least partially non-bioabsorbable, and may be formed from polyester, polyethylene terephthalate (PET), silicone, urethane, combinations thereof, other polymers, and the like. The patch closure may, in some embodiments, be formed in part with a bioabsorbable material and in part with a non-bioabsorbable material. The patch closure may be formed from a woven, knitted, or braided material, a printed material, a molded material, and the like. In an exemplary embodiment, laser cutting a diamond or auxetic pattern into the patch would enable additional stretch such that a highly elastic material is not required.

In some embodiments, at least one polymer coating is applied to the patch in order to reinforce the patch. Depending on the embodiment, the polymer coating is applied to a section of the patch, to multiple sections of the patch, or to the entire patch. Reinforcement polymer coatings may be applied through spray coating or dip coating.

Utilizing an elastic polymer patch and sewing, stitching, or otherwise securing it into the device in a stretched state could help prevent some of the patch bulging after the device is deformed. Other methods for securing/attaching the patch closure to the device frame may include any suitable method, such as by suture, bonding (with other polymers, thermally, via laminating, etc.), welding, adhering, folding and/or trapping the patch closure within the material of the frame, over-molding, any combination thereof, and/or any other suitable attachment mechanism.

In some embodiments a needle is used to apply/secure a suitable suture-, thread-, or yarn-type material to the patch in order to reinforce the patch. Depending on the embodiment, the material is sewn, stitched, adhered, and/or attached to the patch at one point, multiple points, over one section, over multiple sections, or over the entire patch. The suitable suture-, thread-, or yarn-type material used to reinforce the patch may be any suitable biocompatible polymer, or biodegradable/bioresorbable material. In alternative embodiments, suture (or a similar material) may be wrapped around a series of pins in order to form a suitable patterned structure (e.g., a star pattern, cross-hatch pattern, zig-zag pattern, etc.) that will span the desired section(s) (e.g., in the middle of the patch and/or at a distance or distances from center) or the entire patch in order to provide the desired reinforcement to the patch once attached. In some embodiments, reinforcement material (such as a patterned structure) is attached to the patch on an inner surface of the patch (e.g., for a patch positioned within the proximal disc, an inner surface of the patch would be considered as a surface of the patch that is facing the waist of the device as opposed to a surface of the patch facing the proximal disc of the device) such that the material may or may not be completely adhered to the patch. That is, in certain areas/points the reinforcement material may be attached tightly to the patch while in other areas/points the reinforcement material may be more loosely attached. In some embodiments, the patterned structure may be sewn, stitched (e.g., stitched using tack stitches, loop stitches, whip stitches, and any combination thereof), adhered, and or otherwise attached to the patch material using any suitable method in order to reinforce the patch for reinforcing the patch.

This could be used in the event adhering via lamination, and adhesive, or sandwiching it between the patch and another material doesn't work.

b. Patch Support

In some embodiments, the present disclosure is directed to an occlusive medical device comprising a braided frame. The braided frame comprises an annular distal disc portion having a radially outer surface and a radially inner surface, an annular proximal disc portion having a radially outer surface and a radially inner surface, a waist member extending between and connecting the annular distal disc portion to the annular proximal disc portion, and a plurality of braided wire spokes attached to a respective wire group tail and a center markerband on at least one of the annular distal disc portion or the annular proximal disc portion. The radially inner surface of the annular distal disc portion, the waist member, and the radially inner surface of the annular proximal disc portion define an unobstructed passageway through the braided frame.

Figure 11:
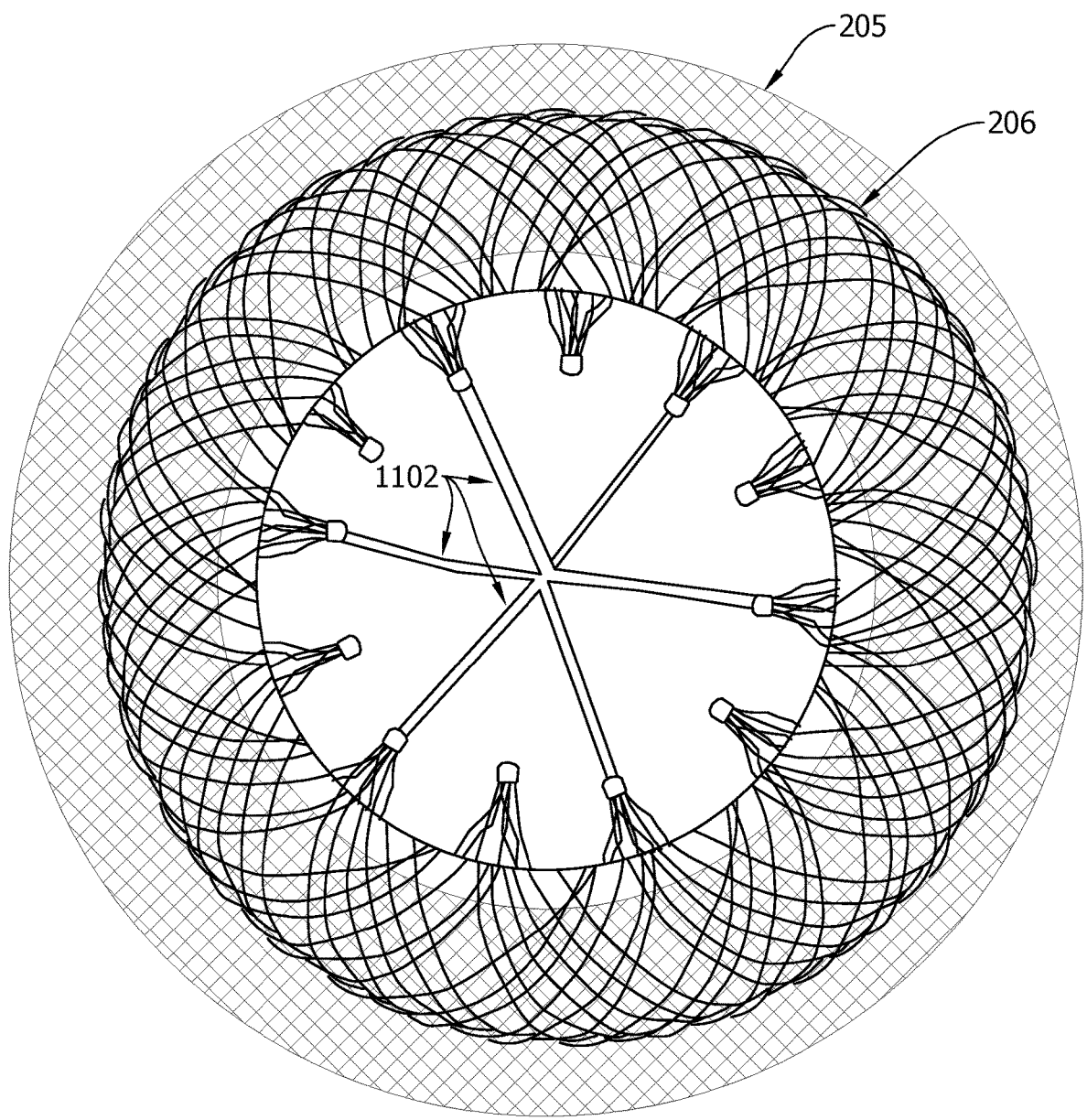
FIG. 11 is an exemplary embodiment of a braided occluder with access passage having a plurality of spokes extending into the center of the access passage in accordance with the present disclosure.

As shown in FIG. 11, spokes 1102 (e.g., Nitinol spokes) formed from the braid wires (3 or more spokes) may be utilized to contain the patch closure and prevent bulging. The nitinol spokes formed from the braid wires increase the radial stiffness of the discs, which may increase the risk of erosion of the atrium. Therefore, in order to reduce the radial stiffness, smaller diameter and/or fewer Nitinol wires or struts can be welded or adhered at the ends of the braid tails before terminating in the center of the device. The shape of the wires may also help reduce the radial stiffness of the disc(s) (see also FIG. 7).

Figure 12:
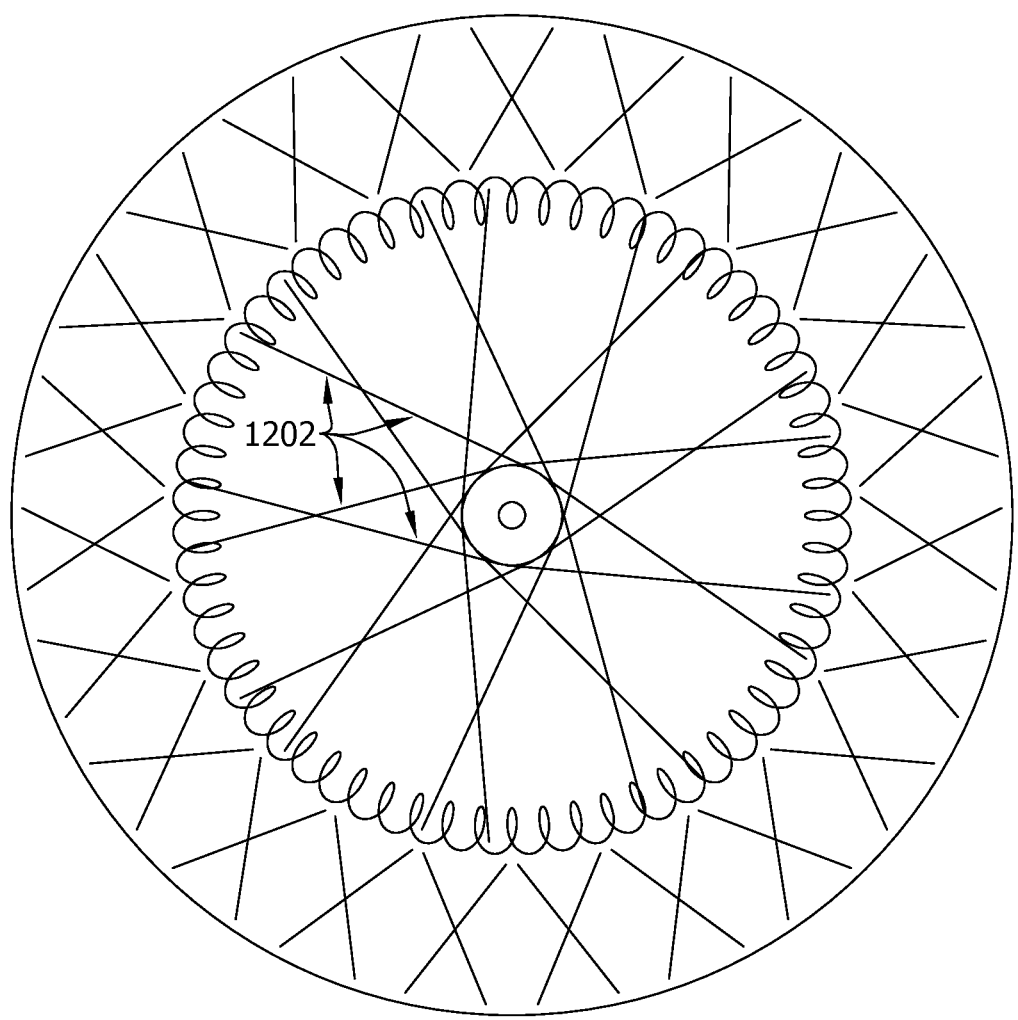
FIG. 12 is an exemplary embodiment of a braided occluder with access passage having a plurality of braid wires extending into the center of the access passage in accordance with the present disclosure.

It is also feasible to route a number of braid wires 1202 (2 or more) from the braid into the middle of the device (FIG. 12). This can be performed on both closed end braid (distal end), and at the braid tails (proximal end). The purpose of these wires 1202 is to contain the patch closure; however, they must have the ability to collapse into the loader or sheath. Braid tails (e.g., Nitinol braid tails) are secured to the patch closure, and the few braid wires 1202 that run to the middle of the device are only used to prevent the patch closure from bulging upon deployment.

Figure 13:
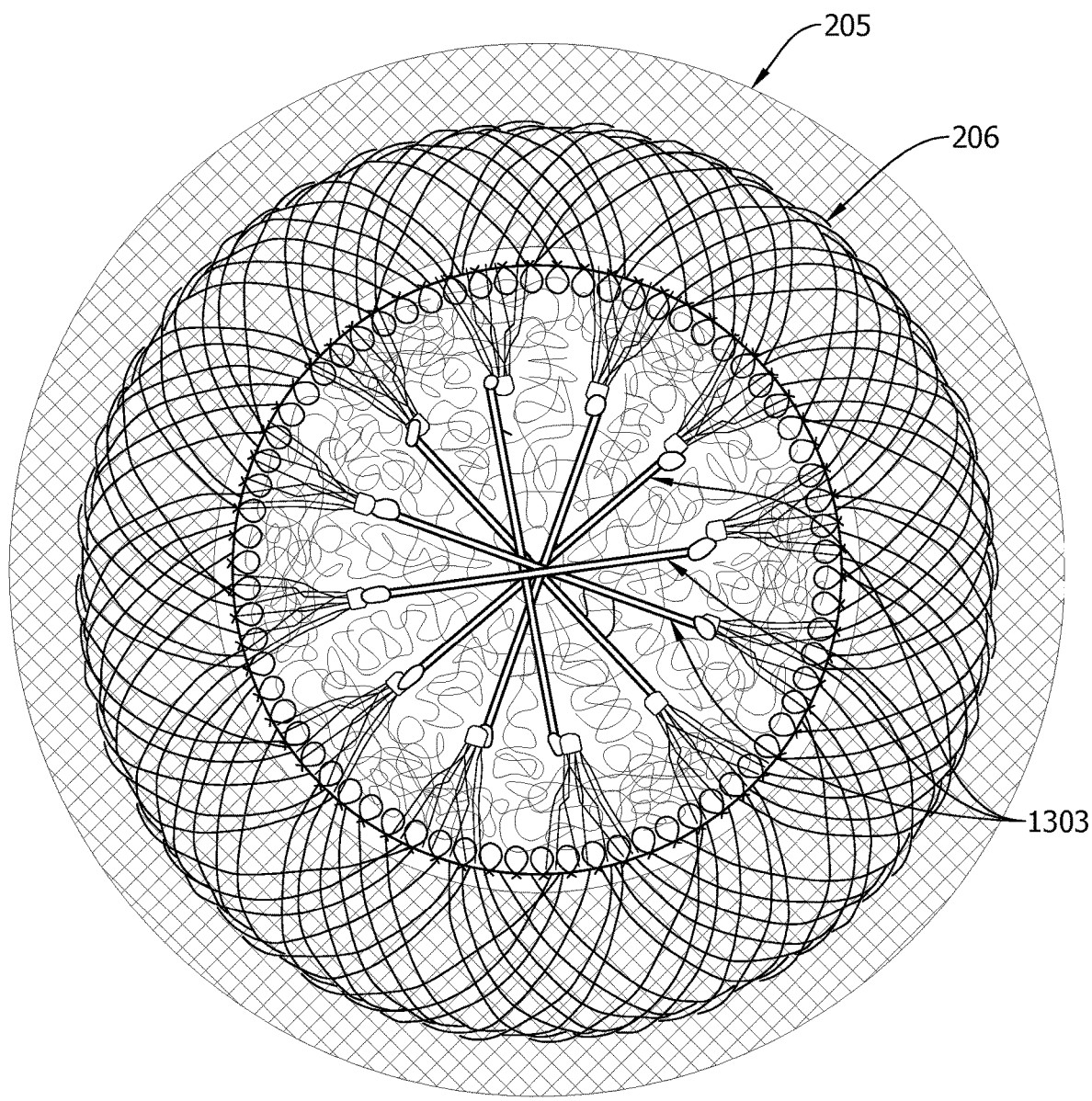
FIG. 13 is an exemplary embodiment of reinforcement material sutured to braid termination points in accordance with the present disclosure.
Figure 14:
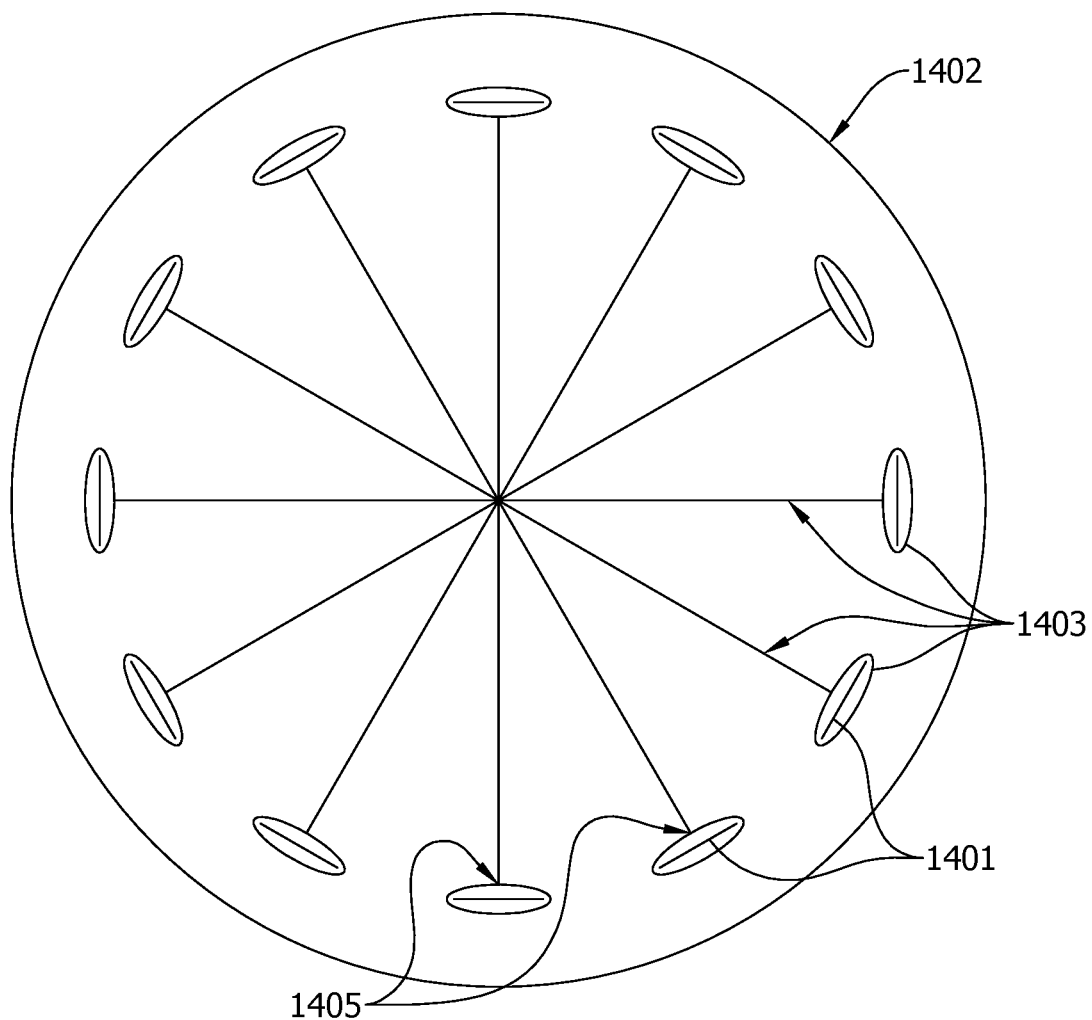
FIG. 14 is an exemplary embodiment of reinforcement material built into patch, in accordance with the present disclosure.

On the proximal end of the braid, a relatively stronger patch material (woven or knitted) may be employed, or a reinforced patch may be employed that is strengthened from the center of the device toward each tail, to facilitate loading and recapture of the device. The reinforced portions of the patch may include any biocompatible polymer or bioresorbable material. Reinforcing the patch provides the ability to use a non-woven low profile patch, similar to the current patch used on Amplatzer™ devices, while strengthening the areas needed for collapsing the device. The reinforcement material may be attached to the inner portion of the patch so the endothelial response is not affected, or it may be attached to the outer portion of the patch if it's deemed necessary for manufacturability. Additionally, the Nitinol braid tails may be tucked into the patch to provide a continuous surface for a uniform healing response. Additionally, the reinforced sections may be attached to the patch material using any suitable method (such as but not limited to being laminated, adhered, or ultrasonically welded to the patch material), and it may extend from the center of the patch all of the way to the OD of the patch, or only to the termination points of the braid. Additionally, the reinforcement material may be sutured to the braid termination points, either using the reinforcement material itself 1303 (FIG. 13), or using a separate piece of suture (not shown). In the embodiment shown in FIG. 14, slit 1401 is formed in patch 1402 and reinforcement material 1403 extends radially from the center and around each slit (thus forming an oval-type shape of reinforcement material 1403 circumscribing each slit 1401) such that each braid termination point (not shown) is tucked into slit 1401 for the sake of providing a continuous surface of the deployed occluder for uniform healing response. The oval-type shape of reinforcement material 1403 provides a strengthened area around each tail and something to tie to so that the patch does not rip when the device is loaded. A separate piece of suture (not shown) may be used near slit 1401 at position 1405 in order to attach reinforcement material 1403 to the braid termination points.

Figure 15:
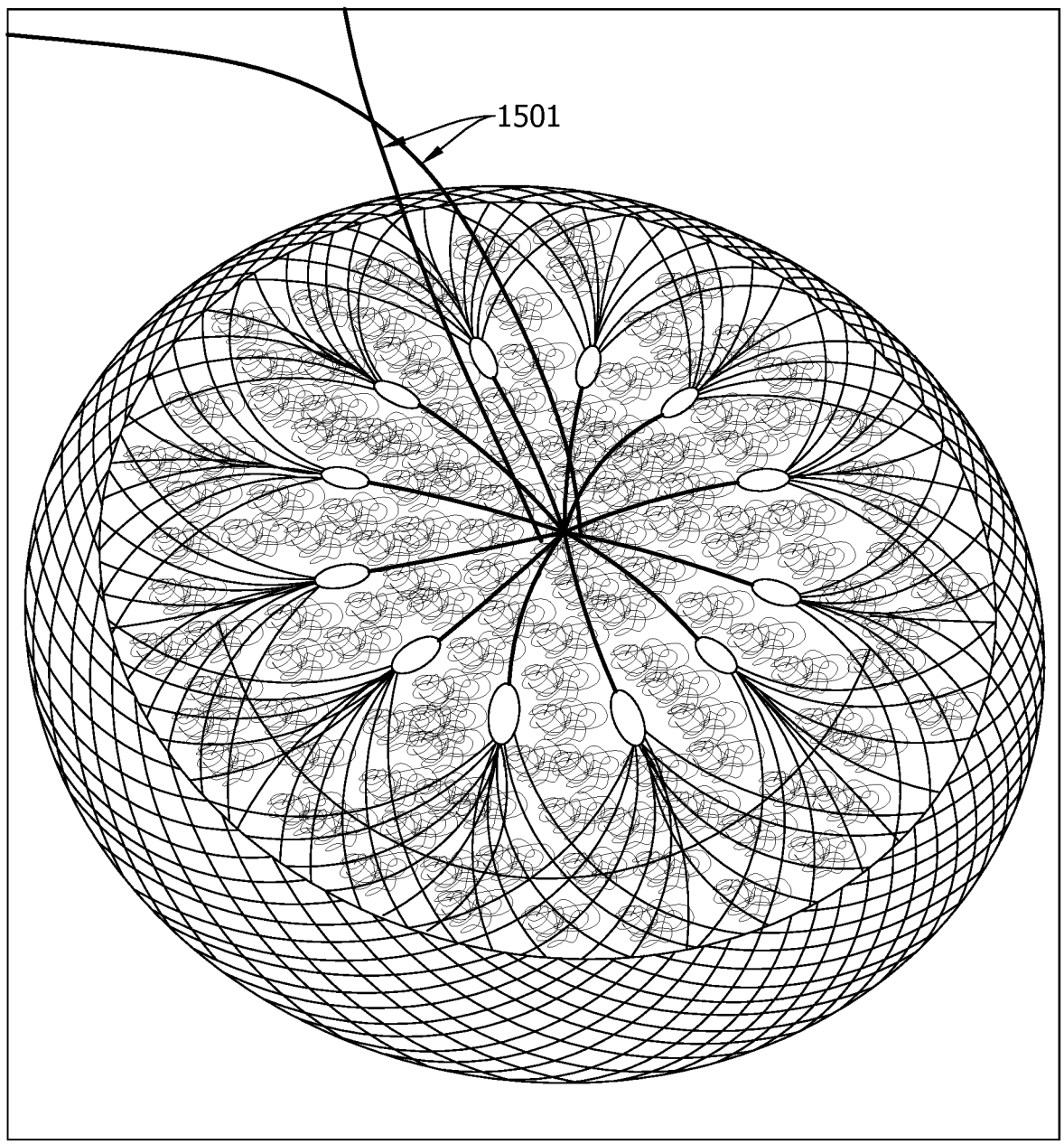
FIG. 15 is an exemplary embodiment of a tether through center of reinforced patch in accordance with the present disclosure.
Figure 16:
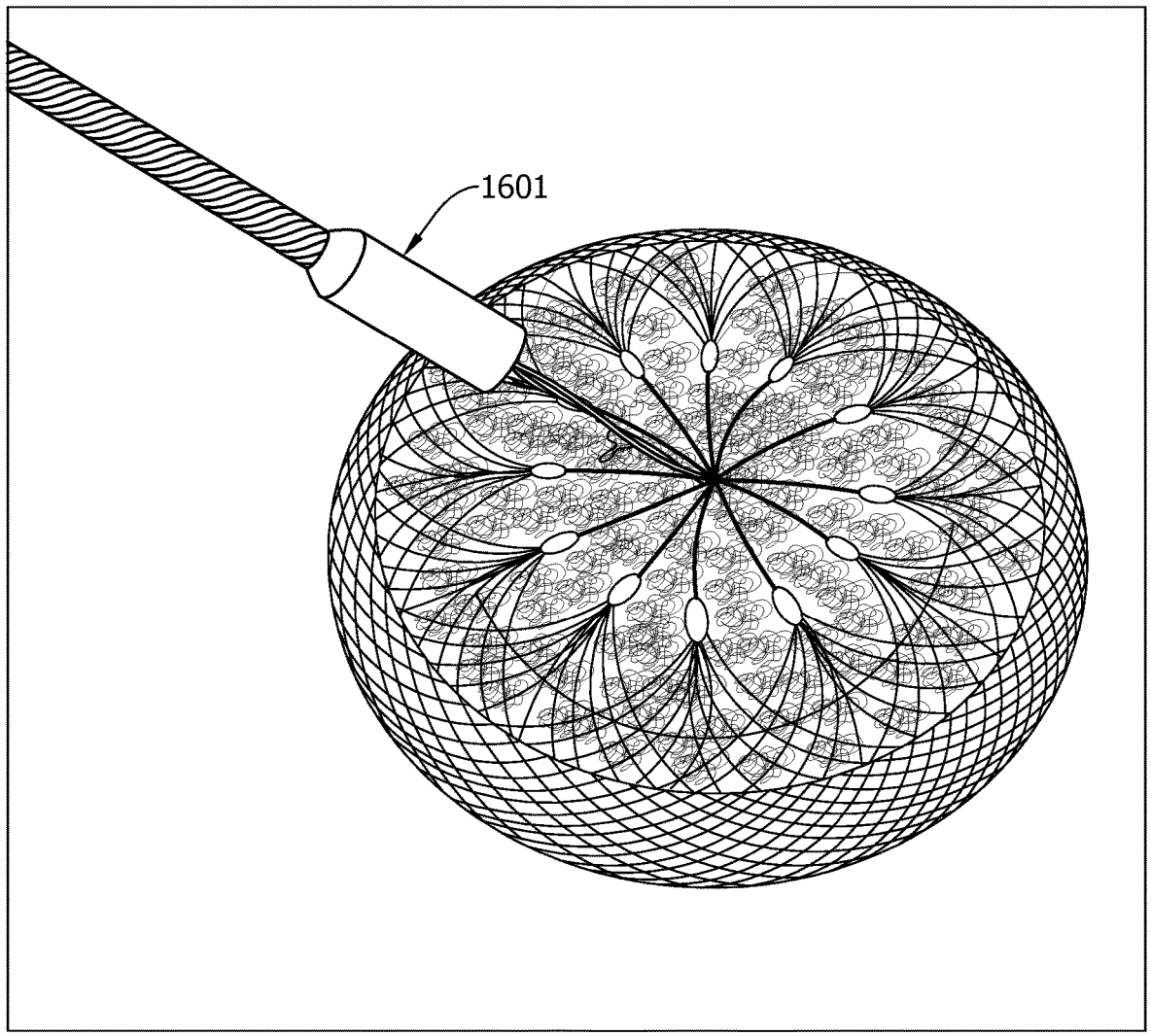
FIG. 16 is an exemplary embodiment of a pusher cable with distal lumen to house reinforced patch in collapsed state in accordance with the present disclosure.

Delivery system attachment to the reinforced patch may include a loop of suture at the center of the reinforced patch, or a hub (e.g., end screw similar to end screw 303, ball and socket, etc.) that is sewn, adhered, laminated, or ultrasonically welded to the reinforced patch. Additionally, the delivery system could consist of a tether 1501 that loops around the middle of the reinforced patch, which would not require any externalized feature on the patch itself (FIG. 15). Lastly, because the reinforced patch is likely to extend beyond the device frame in its collapsed state, and has little column strength for pushability, the delivery system may require a short lumen 1601 built into the pusher mechanism to house the patch material so that the pusher is engaging with the braid frame during advancement (FIG. 16).

c. Methods of Using the Device

In accordance with the present disclosure, the occlusive medical devices disclosed herein are directed toward methods of eliminating or reducing erosion of cardiac tissue. The methods comprise providing an occlusive medical device comprising a braided frame, the braided frame comprising an annular distal disc portion having a radially outer surface and a radially inner surface, an annular proximal disc portion having a radially outer surface and a radially inner surface, and a waist member extending between and connecting the annular distal disc portion to the annular proximal disc portion; wherein the radially inner surface of the annular distal disc portion, the waist member, and the radially inner surface of the annular proximal disc portion define an unobstructed passageway through the braided frame; constraining the occlusive medical device from a preset expanded configuration to a reduced configuration; delivering the occlusive medical device; deploying the occlusive medical device such that the frame returns to the preset expanded configuration; and, increasing the occlusive medical device compliance on cardiac tissue.

It should be understood that any feature of any embodiment disclosed herein may be combined with any other feature. For example, an access passage occluder may include both a polymer coated and closed end braided frame.

In addition, although the occluders of the present disclosure have been described as being suitable for deployment within ASDs, these occluders are suitable for deployment in other tissue and/or defects, including for use for fenestrated ASDs, VSDs, and/or atrial shunting.

While embodiments of the present invention have been described, it should be understood that various changes, adaptations and modifications may be made therein without departing from the spirit of the invention and the scope of the appended claims. For example, it is anticipated that the device body portion could be cylindrical, barrel shaped, concave, convex, tapered, or a combination of shapes without departing from the invention herein. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A method of eliminating or reducing erosion of cardiac tissue, the method comprising:
   providing an occlusive medical device comprising:
      a braided frame comprising:
         an annular distal disc portion having a radially outer surface and a radially inner surface;
         an annular proximal disc portion having a radially outer surface and a radially inner surface; and
         a waist member extending between and connecting the annular distal disc portion to the annular proximal disc portion,
         wherein the radially inner surface of the annular distal disc portion, the waist member, and the radially inner surface of the annular proximal disc portion define an unobstructed passageway through the braided frame; and
         wherein the braided frame is formed with a plurality of formed wires in a closed end braid, each of the plurality of formed wires being attached to a respective wire group tail that extends radially inward past the closed end braid on at least one of the annular distal disc portion or the annular proximal disc portion;
   constraining the occlusive medical device in a reduced configuration;
   delivering the occlusive medical device;
   deploying the occlusive medical device such that the braided frame transitions from the reduced configuration to an expanded configuration; and
   increasing the occlusive medical device compliance on cardiac tissue.

2. The method of claim 1, wherein the closed end braid of the occlusive medical device comprises a closed end braid with loops.

3. The method of claim 1, wherein the occlusive medical device further comprises a plurality of wire loops alternately attached at every other respective wire group tail on at least one of the annular distal disc portion or the annular proximal disc portion.

4. The method of claim 3, wherein the plurality of wire loops comprises nitinol wire loops.

5. The method of claim 1, wherein the occlusive medical device further comprises a center markerband on at least one of the annular distal disc portion or the annular proximal disc portion.

6. The method of claim 1, wherein the braided frame of the occlusive medical device is coated with a polymer coating.

7. The method of claim 6, wherein the polymer coating of the braided frame is a polyurethane coating.

8. The method of claim 1, wherein the braided frame of the occlusive medical device is rolled over onto itself to form two layers of braid on at least one of the annular distal disc portion or the annular proximal disc portion.

9. The method of claim 1, wherein the occlusive medical device further comprises a plurality of braided wire spokes attached to a respective wire group tail and a center markerband on at least one of the annular distal disc portion or the annular proximal disc portion.

10. The method of claim 1, wherein the occlusive medical device further comprises at least one patch closure.

11. The method of claim 10, wherein the at least one patch closure is flexible to transition with the braided frame from the reduced configuration to the expanded configuration.

12. The method of claim 10, wherein one or more sections of the at least one patch closure are coated with a polymer coating.

13. The method of claim 10, wherein one or more portions of the at least one patch closure are reinforced.

14. The method of claim 13, wherein the reinforced portions of the at least one patch closure are reinforced with a biocompatible polymer.

15. The method of claim 13, wherein the reinforced portions of the at least one patch closure are reinforced with a bioresorbable material.

16. The method of claim 13, wherein the reinforced portions of the at least one patch closure are on an inner portion of the at least one patch closure.

17. The method of claim 16, wherein at least one of the reinforced portions of the at least one patch closure are attached tightly to the inner portion of the at least one patch closure.

18. The method of claim 16, wherein at least one of the reinforced portions of the at least one patch closure are attached loosely to the inner portion of the at least one patch closure.

19. The method of claim 10, wherein the at least one patch closure is of an increased penetrability as compared to the braided frame.

20. The method of claim 10, wherein the at least one patch closure comprises an auxetic pattern.

* * * * *